United States Patent [19]

Petzoldt

[11] 4,284,720
[45] Aug. 18, 1981

[54] PROCESS FOR THE PREPARATION OF 19-HYDROXY STEROIDS OF THE ANDROSTANE AND PREGNANE SERIES

[75] Inventor: Karl Petzoldt, Berlin, Fed. Rep. of Germany

[73] Assignee: Schering, A.G., Berlin, Fed. Rep. of Germany

[21] Appl. No.: 112,683

[22] Filed: Jan. 14, 1980

[30] Foreign Application Priority Data

Jan. 12, 1979 [DE] Fed. Rep. of Germany ....... 2901564

[51] Int. Cl.$^3$ ............................................. C12P 33/06
[52] U.S. Cl. ....................................... 435/58; 435/911
[58] Field of Search .......................................... 435/58

[56] References Cited

U.S. PATENT DOCUMENTS

| 2,823,170 | 2/1958 | Muir et al. | 435/60 |
| 3,039,926 | 6/1962 | Shull | 435/58 |

Primary Examiner—Alvin E. Tanenholtz
Attorney, Agent, or Firm—Millen & White

[57] ABSTRACT

10-Methyl steroids of the androstane or pregnane series are converted to the corresponding 19-hydroxy steroid by fermentation with a fungal culture of the genus Nigrospora.

3 Claims, No Drawings

PROCESS FOR THE PREPARATION OF 19-HYDROXY STEROIDS OF THE ANDROSTANE AND PREGNANE SERIES

BACKGROUND OF THE INVENTION

The invention concerns a process for preparing 19-hydroxy-steroids of the androstane and pregnane series.

19-Hydroxy steroids are, as is known, important intermediates for the partial synthesis of pharmacologically active 19-nor steroids. The chemical synthesis of these compounds from the corresponding 10-methyl steroids comprises many stages and is very expensive (J. Amer. Chem. Soc. 84:3204 et seq. [1962] and J. Amer. Chem. Soc. 83:4076 et seq. [1961]). Investigations have also been conducted to hydroxylate 10-methyl steroids in the 19-position by means of microorganism cultures (Bull. Agr. Chem. Japan 22:212 [1958]). However, the previously known methods yield only such low quantities of 19-hydroxy steroids that they are useless from a technical viewpoint.

SUMMARY OF THE INVENTION

In contrast thereto, it is possible with the aid of the process of this invention to convert 10-methyl steroids into the corresponding 19-hydroxy steroids in high yields.

The process comprises fermenting a 10-methyl steroid of the androstane or pregnane series with a fungal culture of the genus Nigrospora. Particularly, this invention provides a process for preparing a 19-hydroxy steroid of the androstane and pregnane series, comprising fermenting the corresponding 10-methyl steroid with a fungal culture of the genus Nigrospora. One useful species is *Nigrospora sphaerica* (A.T.C.C. 12,772).

A process for preparing a 19-hydroxy steroid of the formula

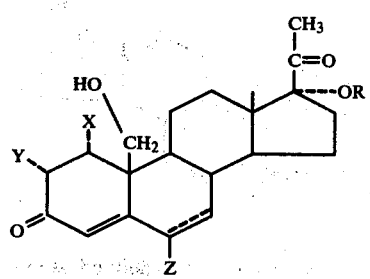

wherein

....... is a single bond or a double bond,

X and Y each is hydrogen or together represent a carbon-carbon bond or a methylene group, Z is hydrogen, fluorine, chlorine or methyl, and R is hydrogen or an acyloxy group of 1-8 carbon atoms, comprises fermenting a 10-methyl steroid of the formula

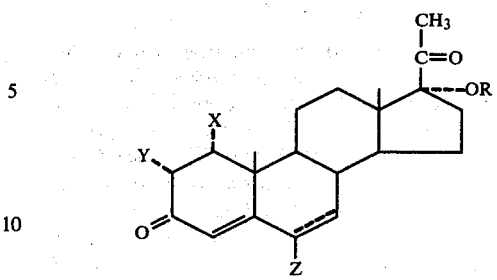

wherein

......, X, Y, Z and R are as defined above, with a fungal culture of the genus Nigrospora.

DETAILED DISCUSSION

The process of this invention is accomplished under the conditions customarily employed in the microbiological hydroxylation of steroids with fungal cultures. Thus, in generally customary preliminary tests, the most favorable fermentation conditions are determined first of all analytically, especially by thin-layer chromatography, for example the selection of the most favorable nutrient medium, the suitable substrate solvent or suspension agent, the substrate concentration, the technical conditions, such as temperature, aeration, pH value, and the optimum times for germination, substrate addition and substrate contact with the enzyme of the microorganism. In this connection, it has been found that it is advantageous to utilize concentrations of about 100–2000 mg of substrate per liter of nutrient medium. The pH is preferably set at a value in the range of 5–7. The cultivation temperature is in the range of 20°–40° C., preferably 25°–35° C. For aeration purposes, 0.5–5 liters of air per minute per liter of culture broth is preferably introduced. The conversion of the substrate is suitably controlled by the analysis of sample extracts using thin-layer chromatography. The duration of fermentation is about 90–100 hours.

After fermentation has been completed, the fermentation products are isolated in a conventional manner. The isolation can be conducted, for example, by extracting the fermentation batches with a water-immiscible organic solvent, such as ethyl acetate, butyl acetate, or methyl isobutyl ketone, concentrating the extracts, and optionally purifying the thus-obtained crude products by chromatography and/or crystallization.

The 10-methyl steroids required as the starting compounds for the process of this invention can be substituted in the usual way. Suitable substituents are, for example, hydroxy groups in the 3β,11β,17α,17β- and/or 21-position, or the esters thereof with alkanecarboxylic acids of 1–8 carbon atoms; oxo groups in the 3,11,17- and/or 20-position; halogen atoms (preferably fluorine atoms or chlorine atoms) in the 6- and/or 9-position; methyl groups in the 6- and/or 16-position; and/or methylene groups in the 1α,2α-, 15α,16α-, 15β,16β-position. The 10-methylcorticoids can be saturated or unsaturated, for example, in the 1,2-, 4,5-, 5,6-, 9,11- and/or 15,16-position.

Preferred 10-methyl steroids are those of general Formula II which can carry as substituent R, for example, a hydrogen atom, a formyloxy group, a propionyloxy group, or a butyryloxy group.

The following examples serve for explaining the process of this invention:

EXAMPLE 1

A 2-liter Erlenmeyer flask containing 500 ml. of a nutrient solution sterilized for 30 minutes at 120° C. in an autoclave and made up of 3% glucose, 1% corn steep liquor, 0.2% NaNO₃, 0.1% KH₂PO₄, 0.2% K₂HPO₄, 0.05% MgSO₄.7H₂O, 0.002% FeSO₄.7H₂O, and 0.05% KCl is inoculated with a lyophilized culture of *Nigrospora sphaerica* and shaken for 72 hours at 30° C. on a rotary shaker. This germination culture serves for inoculating a 20-liter preliminary fermentor charged with 7.5 l. of a nutrient medium sterilized at 121° C. and under 1.1 atmospheres gauge and having the same composition as the germination culture. With the addition of Silicone SH as the antifoaming agent, the culture is now germinated for 36 hours at 29° C. and under a pressure of 0.7 atmosphere gauge under aeration (10 l./min.) and agitation (220 r.p.m.). Thereafter 1.5 l. of this culture is withdrawn under sterile conditions and a primary fermentor having a capacity of 30 liters is inoculated therewith; this fermentor is filled with 23.5 l. of a nutrient medium sterilized as above and consisting of 1% corn steep liquor and 1.25% soybean meal, adjusted to pH 6.2. After a germination phase of 12 hours under preliminary fermentor conditions, 12.5 g. of cyproterone (6-chloro-17α-hydroxy-1α,2α-methylene-4,6-pregnadiene-3,20-dione), dissolved in 300 ml. of dimethylformamide, is added under sterile conditions, and the mixture is further agitated and aerated. The course of the fermentation is controlled by withdrawal of samples which are extracted with methyl isobutyl ketone and analyzed by thin-layer chromatography. After a contact period of 72 hours the conversion of the substrate is completed. The fermentor content is extracted twice with respectively 20 l. of methyl isobutyl ketone; the extracts are combined and first concentrated in a forced circulation evaporator, and then concentrated to dryness at 50° C. bath temperature under vacuum in a rotary evaporator. The residue is dissolved in warm methanol, filtered off from the silicone oil remaining in undissolved form; the filtrate is treated with activated carbon and again evaporated to dryness. The remaining residue (15 g.) is finally crystallized from acetone/diisopropyl ether, thus obtaining 8.8 g. of 6-chloro-17α,19-dihydroxy-1α,2α-methylene-4,6-pregnadiene-3,20-dione, m.p. 215°–216° C.

EXAMPLE 2

Under the conditions of Example 1, 10 g. of megestrol (17α-hydroxy-6-methyl-4,6-pregnadiene-3,20-dione), dissolved in 400 ml. of dimethylformamide, is fermented for 48 hours with a Nigrospora sphaerica culture. After the batch has been worked up and the crude product crystallized from acetone/diisopropyl ether, 6.5 g. of 17α,19-dihydroxy-6-methyl-4,6-pregnadiene-3,20-dione is obtained, m.p. 184°–186° C.

EXAMPLE 3

One gram of 19-hydroxycyproterone (6-chloro-17α,19-dihydroxy-1α,2α-methylene-4,6-pregnadiene-3,20-dione) is dissolved in 7.5 ml. of ethyl acetate; 3 ml. of trifluoroacetic anhydride and 150 mg. of p-toluenesulfonic acid are added thereto, and the mixture is stirred for 15 minutes at room temperature. The reaction mixture is then poured into ice water, the thus-obtained precipitate is vacuum-filtered, washed neutral, and dried. To separate the crude product mixture, the latter is chromatographed over a silica gel column and eluted by means of the solvent gradient methylene chloride-methylene chloride/acetone (8+2):

(a) The fraction I exiting first from the column is evaporated to dryness under vacuum and crystallized from acetone/diisopropyl ether, thus obtaining 560 mg. of 17α,19-diacetoxy-6-chloro-1α,2α-methylene-4,6-pregnadiene-3,20-dione, m.p. 248°–250° C.

(b) The subsequently appearing fraction II is concentrated in the same way and crystallized from acetone/diisopropyl ether to obtain 324 mg. of 17α-acetoxy-6-chloro-19-hydroxy-1α,2α-methylene-4,6-pregnadiene-3,20-dione, m.p. 220°–221° C.

What is claimed is:

1. A process for preparing a 19-hydroxy steroid of the formula

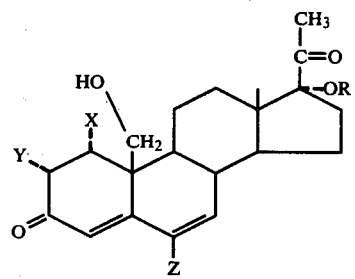

wherein
X and Y each is hydrogen or together represent a carbon-carbon bond or a methylene group,
Z is hydrogen, fluorine, chlorine or methyl, and
R is hydrogen or an acyloxy group of 1–8 carbon atoms,
comprising fermenting at 10-methyl steroid of the formula

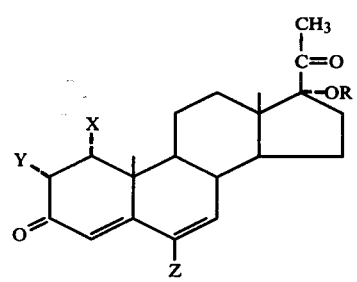

wherein X, Y, Z and R are as defined above, with a fungal culture of the genus Nigrospora and isolating said 19-hydroxy steroid.

2. The process of claim 1, wherein the fungal culture is of the species *Nigrospora sphaerica* (A.T.C.C. 12 772).

3. The process of claim 1, wherein the acyloxy group is $C_{1-8}$ alkanoyloxy.

* * * * *